(12) United States Patent
Miao et al.

(10) Patent No.: US 12,119,114 B2
(45) Date of Patent: Oct. 15, 2024

(54) MISSING MEDICAL DIAGNOSIS DATA IMPUTATION METHOD AND APPARATUS, ELECTRONIC DEVICE AND MEDIUM

(71) Applicant: ZHEJIANG UNIVERSITY, Hangzhou (CN)

(72) Inventors: Xiaoye Miao, Hangzhou (CN); Jianwei Yin, Hangzhou (CN); Yangyang Wu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 315 days.

(21) Appl. No.: 17/874,230

(22) Filed: Jul. 26, 2022

(65) Prior Publication Data

US 2022/0367057 A1    Nov. 17, 2022

Related U.S. Application Data

(63) Continuation of application No. PCT/CN2021/088359, filed on Apr. 20, 2021.

(30) Foreign Application Priority Data

Apr. 19, 2021   (CN) .......................... 202110419669.4

(51) Int. Cl.
G16H 50/20      (2018.01)
G06N 3/0475     (2023.01)

(52) U.S. Cl.
CPC ........... *G16H 50/20* (2018.01); *G06N 3/0475* (2023.01)

(58) Field of Classification Search
None
See application file for complete search history.

(56) References Cited

U.S. PATENT DOCUMENTS

| | | | |
|---|---|---|---|
| 11,757,301 B2 * | 9/2023 | Wu ................... | H02M 7/53873 307/43 |
| 2021/0012244 A1 * | 1/2021 | Taniguchi ................ | G06N 5/04 |
| 2022/0367057 A1 * | 11/2022 | Miao ...................... | G16H 10/60 |
| 2023/0014674 A1 * | 1/2023 | Mouliere ............... | G16H 10/40 |
| 2023/0099113 A1 * | 3/2023 | Ye ...................... | G06V 10/7715 382/155 |
| 2023/0124942 A1 * | 4/2023 | Wu ........................ | H02J 9/062 307/43 |

FOREIGN PATENT DOCUMENTS

CN    111581189 A    8/2020

* cited by examiner

*Primary Examiner* — Kim T Nguyen

(57) ABSTRACT

The present disclosure discloses a missing medical diagnosis data imputation method and apparatus, an electronic device and a medium. The method includes the following steps: acquiring a medical diagnosis data set with data missing; randomly dividing original data into initial sample point data and candidate sample point data, and constructing and training a generative adversarial network initial imputation model by utilizing the initial sample point data; estimating an influence of sample points on a parameter of the generative adversarial network initial imputation model and a prediction result of the generative adversarial network initial imputation model by utilizing an influence function; and sampling a sample point with highest influence among the candidate sample point data by utilizing a binary search algorithm, and further iteratively optimizing the generative adversarial network initial imputation model so as to impute missing data for the medical diagnosis data.

15 Claims, 4 Drawing Sheets

MISSING MEDICAL DIAGNOSIS DATA IMPUTATION METHOD AND APPARATUS, ELECTRONIC DEVICE AND MEDIUM

CROSS REFERENCE OF RELATED APPLICATIONS

The present application claims priority of International Patent Application No. PCT/CN2021/088359, filed on Apr. 20, 2021, which claims priority of Chinese Patent Application No. 202110419669.4, filed on Apr. 19, 2021, the entire contents of which are hereby incorporated by reference.

TECHNICAL FIELD

The present disclosure relates to the database imputation technology, and particularly to a missing medical diagnosis data imputation method and apparatus, an electronic device and a medium.

BACKGROUND

Data missing is a problem with which medical diagnosis data often faces. Main reasons for the data missing can include:
(a) instable working state of a medical detection instrument, that is, on-site environmental factors or human reasons cause the medical detection instrument not to work normally within a certain period of time, resulting in the data missing; and
(b) medical monitoring data, that is, in a medical monitoring process, abnormal monitoring data generally occurs due to reasons such as accuracy of the detection instrument, abnormal fluctuation during production and the like. Such "poor data" does not match actual production conditions and needs to be eliminated, but such an elimination process means cause of the data missing.

The medical data missing will result in incomplete data information, which directly affects the later medical diagnosis. Therefore, it is necessary to impute missing data for the medical diagnosis data to improve the integrity of the data, thereby improving the quality of the data analysis in later medical diagnosis.

It is well known that imputing date for the medical diagnosis data with the data missing is an effective way to improve the integrity of the data. However, due to high model complexity of a traditional imputation method, medical diagnosis data cannot be processed directly and effectively. At present, scholars at home and abroad have done some work on the problem of missing data imputation, but these works still have limitations as follows: (1) the imputation effect of the data imputation method is limited; and (2) the data imputation method is highly complex and is incapable of processing the missing data.

SUMMARY

An objective of the present disclosure is to provide a missing medical diagnosis data imputation method and apparatus, an electronic device and a medium, so as to solve the problem that it is difficult for the traditional imputation method to process missing medical diagnosis data and effectively impute missing data for the medical diagnosis data, so as to improve the integrity of medical data as much as possible.

In order to achieve the above objective, the present disclosure adopts the following technical solutions.

According to a first aspect, an embodiment of the present disclosure provides a missing medical diagnosis data imputation method, including:
acquiring raw data with data missing, wherein the raw data is a medical diagnosis dataset with the data missing;
randomly dividing the original data into initial sample point data and candidate sample point data, and constructing and training a generative adversarial network initial imputation model by utilizing the initial sample point data;
estimating a change in a parameter of the generative adversarial network initial imputation model by sample points in the candidate sample point data;
on the basis of the change in the parameters of the model, calculating an influence of the sample points in the candidate sample point data on a prediction result of the generative adversarial network initial imputation model by utilizing a chain rule;
estimating the prediction result of the adversarial network initial imputation model by utilizing the influence;
sampling a sample point with highest influence in the candidate sample point data by utilizing a binary search algorithm, and further iteratively optimizing the generative adversarial network initial imputation model to obtain a generative adversarial network imputation model; and
imputing missing data for the medical diagnosis data by utilizing the generative adversarial network imputation model.

According to a second aspect, an embodiment of the present disclosure provides a missing medical diagnosis data imputation apparatus, including:
an acquisition module, configured to acquire raw data with data missing, wherein the raw data is a medical diagnosis dataset with the data missing;
a construction module, configured to randomly divide the original data into initial sample point data and candidate sample point data, and construct and train a generative adversarial network initial imputation model by utilizing the initial sample point data;
a parameter estimation module, configured to estimate a change in a parameter of the generative adversarial network initial imputation model by sample points in the candidate sample point data by utilizing an influence function;
an influence evaluation module, configured to calculate an influence of the sample points in the candidate sample point data on a prediction result of the generative adversarial network initial imputation model by utilizing a chain rule on the basis of the change in the parameters of the model;
a result prediction module, configured to estimate the prediction result of the adversarial network initial imputation model by utilizing the influence;
a sampling module, configured to sample a sample point with highest influence in the candidate sample point data by utilizing a binary search algorithm, and further iteratively optimizing the generative adversarial network initial imputation model to obtain a generative adversarial network imputation model; and
a generation module, configured to impute missing data for the medical diagnosis data by utilizing the generative adversarial network imputation model.

According a third aspect, an embodiment of the present disclosure provides an electronic device, including:
one or more processors;
a memory, configured to store one or more programs;
the one or more programs, when executed by the one or more processors, cause the one or more processors to implement the method as described in the first aspect.

According to a fourth aspect, an embodiment of the present disclosure provides a non-transitory computer-readable storage medium storing a computer program, wherein the program, when executed by a processor, implements the method described in the first aspect.

According to the above technical solutions, the embodiment of the present disclosure constructs and trains the generative adversarial network initial imputation model. The present disclosure estimates the change in the parameter of the generative adversarial network initial imputation model by sample points in the candidate sample point data by utilizing an influence function. On the basis of the change in the parameter of the model, the present disclosure calculates the influence of the sample points in the candidate sample point data on the prediction result of the generative adversarial network initial imputation model by utilizing the chain rule. The present disclosure estimates the prediction result of the adversarial network initial imputation model by utilizing the influence. The present disclosure samples the sample point with highest influence in the candidate sample point data by utilizing the binary search algorithm, and further iteratively optimizes the generative adversarial network initial imputation model to obtain the generative adversarial network imputation model, so as to impute missing data for the medical diagnosis data. Under the condition of ensuring the imputation accuracy of the model, the imputation method can greatly reduce training samples and training time required by the model in a fashion of sampling the sample point with highest influence, and thus greatly enhancing the practicability of the imputation model and the efficiency of processing large-scale missing data.

BRIEF DESCRIPTION OF THE DRAWINGS

Accompanying drawings described herein are used to provide further understanding of the present disclosure and constitute a part of the present disclosure. Exemplary embodiments of the present disclosure and their descriptions are used to explain the present disclosure and do not constitute an improper limitation of the present disclosure. In the drawings.

DESCRIPTION OF THE EMBODIMENTS

Now, technical solutions of the present disclosure will be further described with reference to accompanying drawings and specific implementations.

First Embodiment

Figure 1:
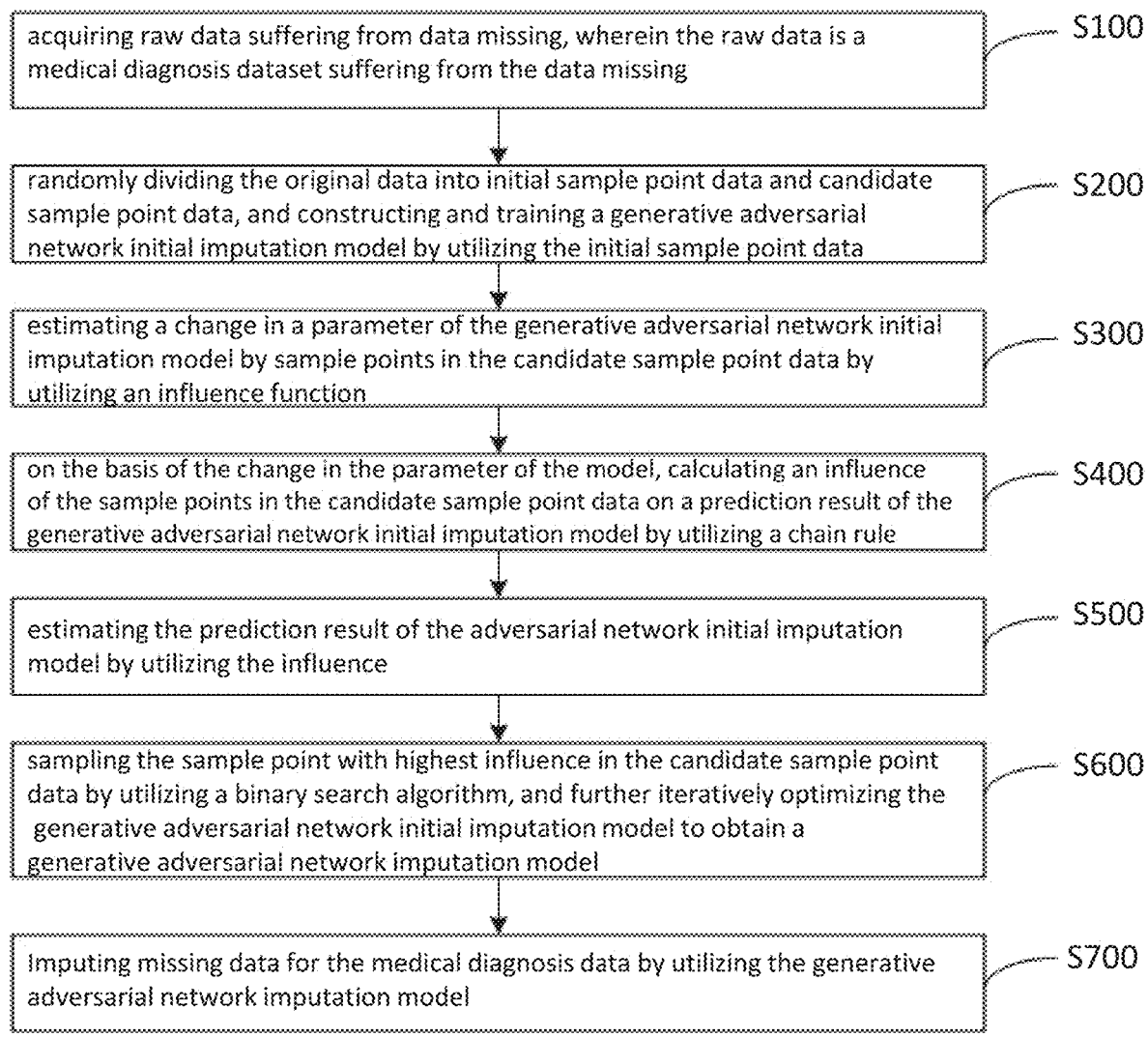
FIG. 1 is a flowchart of a missing medical diagnosis data imputation method according to an embodiment of the present disclosure.

FIG. 1 is a flowchart of a missing medical diagnosis data imputation method according to an embodiment of the present disclosure. The method includes the following steps.

Step S100, acquiring raw data with data missing, wherein the raw data is a medical diagnosis dataset with the data missing.

The medical diagnosis data set with the data missing may specifically include data collected from medical instruments such as an artificial respirator, a heart sound sensor and a hemoglobin meter. The data missing in the medical diagnosis data is caused by diagnosis data missing when the medical diagnosis instrument breaks down.

Step S200, randomly dividing the original data into initial sample point data and candidate sample point data, and constructing and training a generative adversarial network initial imputation model by utilizing the initial sample point data. This step may include the following substeps.

Substep S201, calculating and obtaining a missing matrix M corresponding to a data missing state in the original data X based on the acquired original data X, wherein when a feature of the original data X exists, the missing state of a corresponding position in the missing matrix M is 1; and when the feature of the data matrix X is missing, the missing state of the corresponding position in the missing matrix M is 0.

Substep S202, dividing the original data X into initial sample point data $X^o$ and candidate sample point data $X^c$.

Substep S203, constructing and training a generative adversarial network initial imputation model based on the initial sample point data $X^o$.

Specifically, the adversarial network initial imputation model includes a generator model G and a discriminator model D, wherein the generator model G is configured to impute missing data for the initial sample point data $X^o$, and input the imputed data into the discriminator model D; and wherein the discriminator model D is configured to discriminate the imputed data from the initial sample point data $X^o$ to the greatest extent. The generator model and the discriminator model are both deep neural network structures composed of various activation functions.

Training strategies for the generator model and the discriminator model are described as follows.

The training strategy of the generator model is described as follows.

A parameter of a current discriminator model D is fixed, and the generator model G is trained according to an autoencoder loss function in the generator model G and a feedback of the discriminator model D on a discrimination result of the data generated by the generator model G, such that a training process of the generator model G is described as follows.

Firstly, a random Gaussian noise matrix Z is generated based on a size of an original data matrix, and the data matrix $X^o$ is initialized by utilizing the random Gaussian noise matrix Z to obtain a noise imputation matrix $X^{(z)}$:

$$X^{(z)} = X^o \otimes M + Z \otimes (1-M) \tag{1}$$

wherein $\otimes$ denotes an element-wise multiplication notation.

Secondly, the noise imputation matrix $X^{(z)}$ is input into the generator model G. A loss function L of the generator model includes a reconstruction loss function $L_{rec}$ and a discrimination result feedback function $L_{pro}$ of the discriminator model, as shown below:

$$L = -E[(1-M) \otimes \log(D(\hat{X}))] + \lambda E[M \otimes (X^o - \hat{x})^2] \tag{2}$$

wherein a hyperparameter λ is used to weigh the generator model, $\hat{X}$ represents a imputation matrix output by the generator model G after imputation of the original data, and $D(\hat{X})$ represents a probability that each feature of all samples in predicting the imputation matrix $\hat{X}$ by the discriminator model D belongs to an real feature.

Finally, the generator model G performs model training by minimizing its loss function to obtain a parameter of a current optimal generator model.

The training strategy of the discriminator model is described as follows.

The parameter of the current generator model is fixed; and by using the imputation matrix $\hat{X}$ output by the trained generator model G after imputation of the original data as an input of the discriminator model D, the discriminator model D determines the probability that each feature in all samples belongs to the real feature. Therefore, a formula for calculating the loss function of the discriminator model D is described as follows:

$$L_D = -E[M \otimes \log(D(\hat{X})) + (1-M) \otimes \log(1-D(\hat{X}))] \quad (3)$$

the discriminator model D is trained by minimizing the loss function $L_D$ to obtain a parameter of a current optimal discriminator model.

The training strategies of the generator model and the discriminator model are repeated by utilizing a batch training method until the maximum number of iterations of the model is reached, such that the adversarial network initial imputation model is finally obtained.

Figure 2:
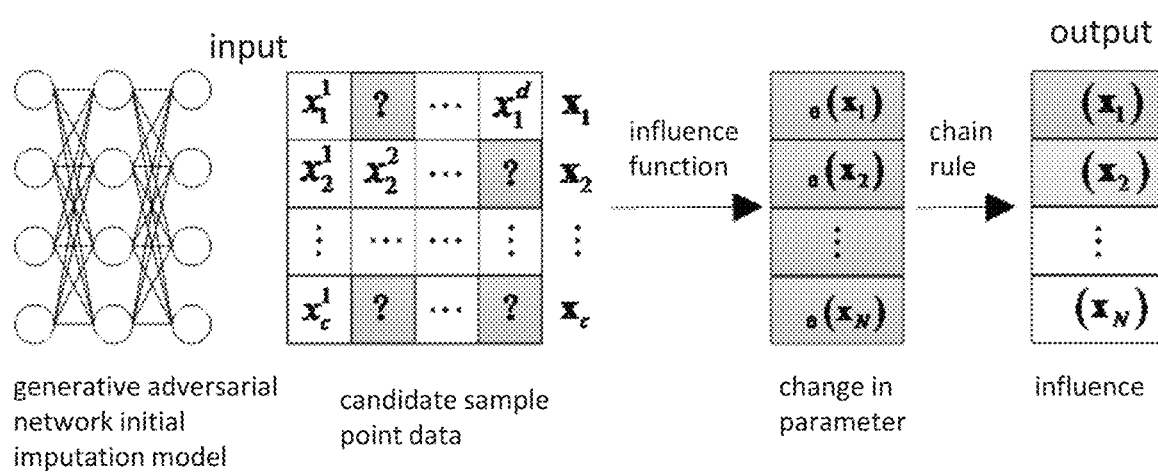
FIG. 2 is a block diagram of a method for evaluating an influence of sample point data by utilizing an influence function according to an embodiment of the present disclosure.

Step S300, estimating a change in the parameter of the generative adversarial network initial imputation model by sample points in the candidate sample point data by utilizing an influence function. FIG. 2 is a block diagram of a method for evaluating an influence of sample point data by utilizing an influence function according to the present disclosure.

Specifically, calculating a change in a parameter of an initial imputation model by utilizing the influence function $I_\theta(x)$ when each sample x is added to an initial training set:

$$I_\theta(x) = \nabla \nabla^{-1} L(X^0, M, \bar{\theta}) \cdot \nabla L(\{x\}, \{m\}, \hat{\theta}) \quad (4)$$

wherein $\nabla \nabla L(X^0, M, \hat{\theta})$ represents a Hessian matrix of the model, and $\nabla L(\{x\}, \{m\}, \hat{\theta})$ represents a gradient of the model corresponding to a loss function of the model when a sample point x is calculated.

Step S400, on the basis of the change in the parameter of the model, calculating an influence of the sample points in the candidate sample point data on a prediction result of the generative adversarial network initial imputation model by utilizing a chain rule.

Specifically, on the basis of the change in the parameter of the model, the influence I(x) of the sample point is calculated by utilizing the chain rule, that is, the initial imputation model predicts the change in the loss function on a validation set H (with its mask matrix $M^H$):

$$I(x) = \nabla L(H, M^H, \hat{\theta})^T \cdot I_\theta(x) \quad (5)$$

Step S500, evaluating the prediction result of the adversarial network initial imputation model by utilizing the influence.

Specifically, the influence I(x) of all sample points is utilized to estimate that the imputation model predicts the loss function on the validation set H when being trained by utilizing all data sample points, $$\hat{L}(X^c, H) = L(H, M^H, X^0) - \frac{1}{N}\sum_{x \in X^c} I(x) \quad (6)$$

Step S600, sampling the sample point with highest influence in the candidate sample point data by utilizing a binary search algorithm, and further iteratively optimizing the generative adversarial network initial imputation model to obtain a generative adversarial network imputation model.

Specifically, a minimum set $X^{n*}$ of sample points with highest influence is retrieved by utilizing a binary search algorithm, and moreover, it is ensured that the model obtained by training the $X^{n*}$ predicts the loss function on the validation set H, that is, $$\hat{L}(X^{n*}, H) \leq \hat{L}(X^c, H) \leq \hat{L}(X^{n*-1}, H) \quad (7)$$

based on this, the generative adversarial network initial imputation model is further iteratively optimized to obtain a generative adversarial network imputation model.

Step S700, imputing missing data for the medical diagnosis data by utilizing the generative adversarial network imputation model.

It can be seen from the above embodiment that the embodiment of the present disclosure constructs and trains the generative adversarial network initial imputation model. The present disclosure estimates the change in the parameter of the generative adversarial network initial imputation model by sample points in the candidate sample point data by utilizing the influence function. On the basis of the change in the parameter of the model, the present disclosure calculates the influence of the sample points in the candidate sample point data on the prediction result of the generative adversarial network initial imputation model by utilizing the chain rule. The present disclosure estimates the prediction result of the adversarial network initial imputation model by utilizing the influence. The present disclosure samples the sample point with highest influence in the candidate sample point data by utilizing the binary search algorithm, and further iteratively optimizes the generative adversarial network initial imputation model to obtain the generative adversarial network imputation model, so as to impute missing data for the medical diagnosis data. Under the condition of ensuring the imputation accuracy of the model, the imputation method can greatly reduce training samples and training time required by the model by means of sampling the sample point with highest influence, and thus greatly enhancing the practicability of the imputation model and the efficiency of processing large-scale missing data.

Figure 3:
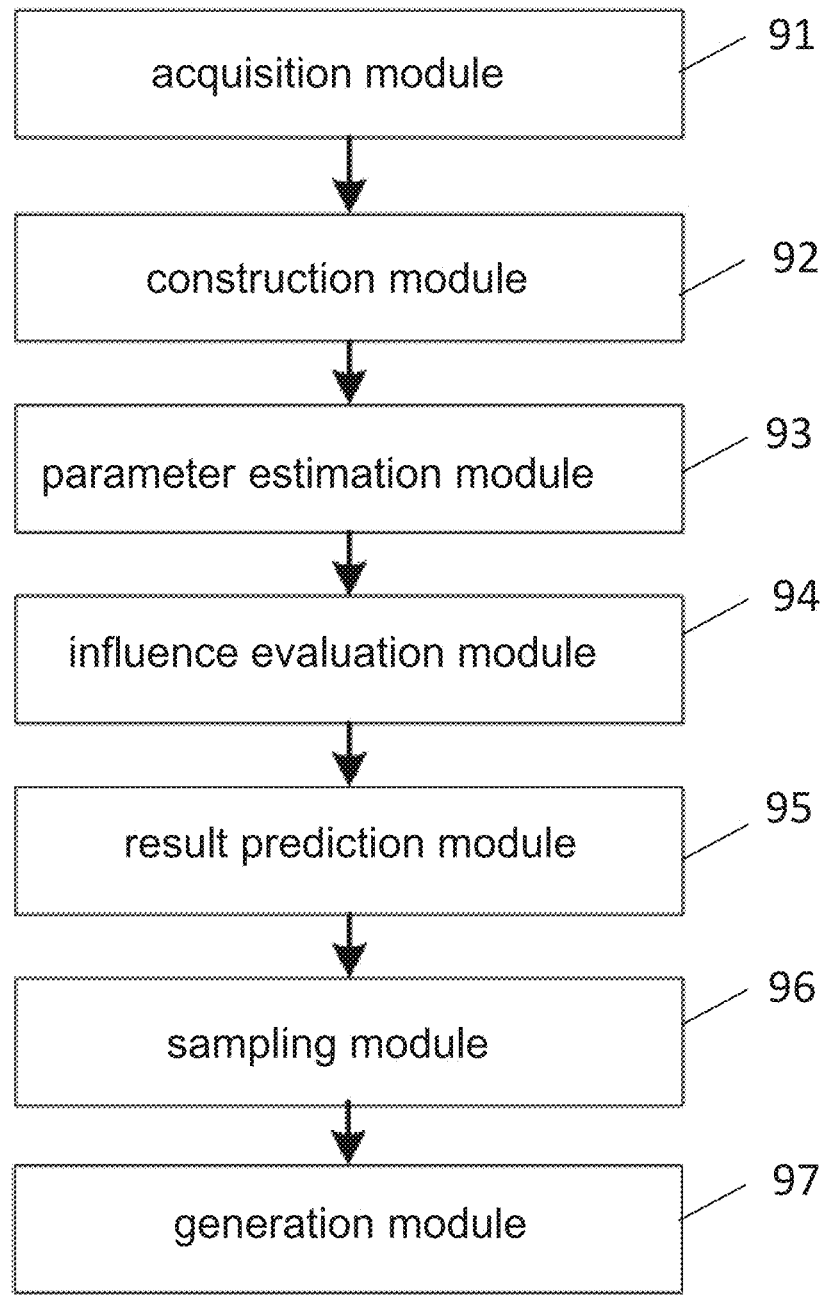
FIG. 3 is a block diagram of a missing medical diagnosis data imputation apparatus according to an embodiment of the present disclosure.
Figure 4:
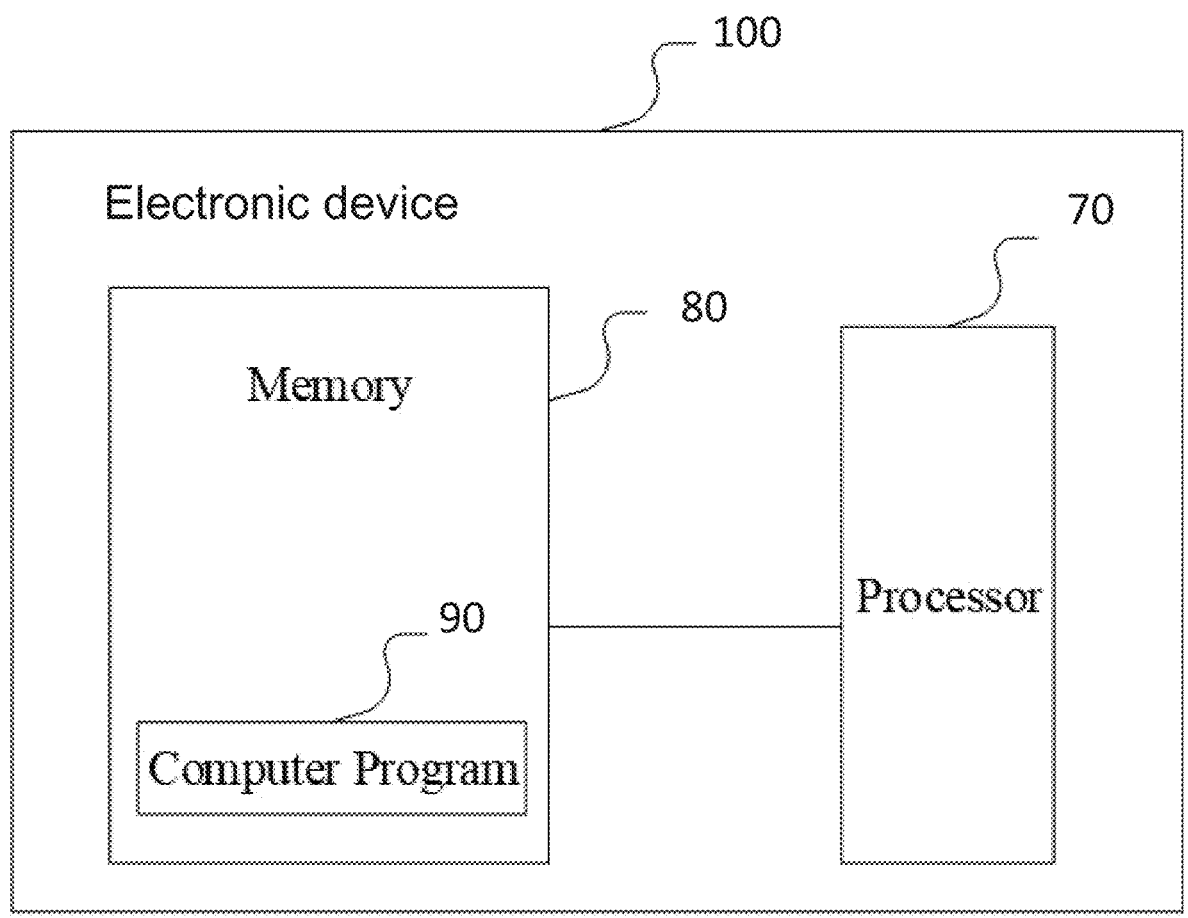
FIG. 4 is a block diagram of an electronic device according to an embodiment of the present disclosure.

The present disclosure further provides an embodiment of a missing medical diagnosis data imputation apparatus, corresponding to the foregoing embodiment of the missing medical diagnosis data imputation method, FIG. 3 is a block diagram of a missing medical diagnosis data imputation apparatus according to an exemplary embodiment. With reference to FIG. 3, the apparatus includes:

an acquisition module 91, configured to acquire raw data with data missing, wherein the raw data is a medical diagnosis dataset with the data missing;

a construction module 92, configured to randomly divide the original data into initial sample point data and candidate sample point data, and construct and train a generative adversarial network initial imputation model by utilizing the initial sample point data;

a parameter estimation module 93, configured to estimate a change in a parameter of the generative adversarial network initial imputation model by sample points in the candidate sample point data by utilizing an influence function;

an influence evaluation module 94, configured to calculate an influence of the sample points in the candidate sample point data on a prediction result of the generative adversarial network initial imputation model by utilizing a chain rule on the basis of the change in the parameter of the model;

a result prediction module 95, configured to estimate the prediction result of the adversarial network initial imputation model by utilizing the influence;

a sampling module 96, configured to sample a sample point with highest influence in the candidate sample point data by utilizing a binary search algorithm, and further iteratively optimize the generative adversarial network initial imputation model to obtain a generative adversarial network imputation model, and a generation module 97, configured to impute missing data for the medical diagnosis data by utilizing the generative adversarial network imputation model obtained from the training.

Regarding the apparatus in the above-mentioned embodiment, a specific manner in which each module performs an operation has been described in detail in the embodiment of the method, and will not be described in detail here.

Regarding the embodiment of the apparatus, as it substantially corresponds to the embodiment of the method, reference may be made to the partial description of the embodiment of the method for related parts. The embodiment of the apparatus described above is only illustrative, wherein units described as separate components may or may not be physically separated, and components presented as units may or may not be physical units, that is, they may be co-located, or can be distributed over multiple network elements. Some or all of the modules can be selected according to actual needs to achieve the objective of the solutions of the present disclosure. Those ordinarily skilled in the art can understand and implement the solutions without any creative effort.

Accordingly, the present disclosure further provides an electronic device 100, including one or more processors 70; and a memory 80, configured to store one or more programs 90, wherein when the one or more programs 90 are executed by the one or more processors 70, the one or more processors 70 implement the missing medical diagnosis data imputation method mentioned above. The memory 80 is a non-transitory memory.

Accordingly, the present disclosure further provides a computer-readable storage medium on which a computer instruction is stored, wherein the instruction, when executed by a processor, implements the missing medical diagnosis data imputation method mentioned above.

The above is a preferred embodiment of the present disclosure. It should be noted that for those skilled in the art, several improvements and modifications can be made without departing from the principle of the present disclosure. These improvements and modifications should be considered to fall within a protective scope of the present disclosure.

What is claimed is:

1. A missing medical diagnosis data imputation method, comprising:

acquiring raw data with data missing, wherein the raw data is a medical diagnosis dataset with the data missing;

randomly dividing the original data into initial sample point data and candidate sample point data, and constructing and training a generative adversarial network initial imputation model by utilizing the initial sample point data;

estimating a change in a parameter of the generative adversarial network initial imputation model by sample points in the candidate sample point data;

on the basis of the change in the parameter of the model, calculating an influence of the sample points in the candidate sample point data on a prediction result of the generative adversarial network initial imputation model by utilizing a chain rule;

estimating the prediction result of the adversarial network initial imputation model by utilizing the influence;

sampling a sample point with highest influence in the candidate sample point data by utilizing a binary search algorithm, and further iteratively optimizing the generative adversarial network initial imputation model to obtain a generative adversarial network imputation model; and imputing missing data for the medical diagnosis data by utilizing the generative adversarial network imputation model.

2. The missing medical diagnosis data imputation method according to claim 1, wherein the adversarial network initial imputation model comprises a generator model and a discriminator model, wherein the generator model is configured to impute missing date for the initial sample point data, and input the imputed data into the discriminator model; and the discriminator model is configured to discriminate the imputed data from the initial sample point data to the greatest extent.

3. The missing medical diagnosis data imputation method according to claim 2, wherein the generator model and the discriminator model are both deep neural network structures composed of various activation functions.

4. The missing medical diagnosis data imputation method according to claim 3, wherein the generator model is trained according to a reconstruction loss function in the generator model and a feedback of the discriminator model on a discrimination result of the data generated by the generator model.

5. The missing medical diagnosis data imputation method according to claim 1, wherein the step of "randomly dividing the original data into initial sample point data and candidate sample point data, and constructing and training a generative adversarial network initial imputation model by utilizing the initial sample point data" comprises:

calculating and obtaining a missing matrix corresponding to a data missing state in the original data based on the acquired original data, wherein when a feature of the original data exists, the missing state of a corresponding position in the missing matrix is 1; and when the feature of the data matrix is missing, the missing state of the corresponding position in the missing matrix is 0;

dividing the original data into initial sample point data and candidate sample point data; and constructing and training a generative adversarial network initial imputation model based on the initial sample point data.

6. An electronic device, comprising:

one or more processors;

a memory, configured to store one or more programs;

the one or more programs, when executed by the one or more processors, cause the one or more processors to implement a method comprising:

acquiring raw data with data missing, wherein the raw data is a medical diagnosis dataset with the data missing;

randomly dividing the original data into initial sample point data and candidate sample point data, and constructing and training a generative adversarial network initial imputation model by utilizing the initial sample point data;

estimating a change in a parameter of the generative adversarial network initial imputation model by sample points in the candidate sample point data;

on the basis of the change in the parameter of the model, calculating an influence of the sample points in the candidate sample point data on a prediction result of the generative adversarial network initial imputation model by utilizing a chain rule;

estimating the prediction result of the adversarial network initial imputation model by utilizing the influence;

sampling a sample point with highest influence in the candidate sample point data by utilizing a binary search algorithm, and further iteratively optimizing the generative adversarial network initial imputation model to obtain a generative adversarial network imputation model; and imputing missing data for the medical diagnosis data by utilizing the generative adversarial network imputation model.

7. The electronic device according to claim 6, wherein the adversarial network initial imputation model comprises a generator model and a discriminator model, wherein the generator model is configured to impute missing data for the initial sample point data, and input the imputed data into the discriminator model; and the discriminator model is configured to discriminate the imputed data from the initial sample point data to the greatest extent.

8. The electronic device according to claim 7, wherein the generator model and the discriminator model are both deep neural network structures composed of various activation functions.

9. The electronic device according to claim 8, wherein the generator model is trained according to a reconstruction loss function in the generator model and a feedback of the discriminator model on a discrimination result of the data generated by the generator model.

10. The electronic device according to claim 6, wherein the step of "randomly dividing the original data into initial sample point data and candidate sample point data, and constructing and training a generative adversarial network initial imputation model by utilizing the initial sample point data" comprises:

calculating and obtaining a missing matrix corresponding to a data missing state in the original data based on the acquired original data, wherein when a feature of the original data exists, the missing state of a corresponding position in the missing matrix is 1; and when the feature of the data matrix is missing, the missing state of the corresponding position in the missing matrix is 0;

dividing the original data into initial sample point data and candidate sample point data; and constructing and training a generative adversarial network initial imputation model based on the initial sample point data.

11. A non-transitory computer-readable storage medium storing a computer program, wherein the program, when executed by a processor, implements a method comprising:

acquiring raw data with data missing, wherein the raw data is a medical diagnosis dataset with the data missing;

randomly dividing the original data into initial sample point data and candidate sample point data, and constructing and training a generative adversarial network initial imputation model by utilizing the initial sample point data;

estimating a change in a parameter of the generative adversarial network initial imputation model by sample points in the candidate sample point data;

on the basis of the change in the parameter of the model, calculating an influence of the sample points in the candidate sample point data on a prediction result of the generative adversarial network initial imputation model by utilizing a chain rule;

estimating the prediction result of the adversarial network initial imputation model by utilizing the influence;

sampling a sample point with highest influence in the candidate sample point data by utilizing a binary search algorithm, and further iteratively optimizing the generative adversarial network initial imputation model to obtain a generative adversarial network imputation model; and imputing missing data for the medical diagnosis data to be imputed by utilizing the generative adversarial network imputation model.

12. The non-transitory computer-readable storage medium according to claim 11, wherein the adversarial network initial imputation model comprises a generator model and a discriminator model, wherein the generator model is configured to impute missing data for the initial sample point data, and input the imputed data into the discriminator model; and the discriminator model is configured to discriminate the imputed data from the initial sample point data to the greatest extent.

13. The non-transitory computer-readable storage medium according to claim 12, wherein the generator model and the discriminator model are both deep neural network structures composed of various activation functions.

14. The non-transitory computer-readable storage medium according to claim 13, wherein the generator model is trained according to a reconstruction loss function in the generator model and a feedback of the discriminator model on a discrimination result of the data generated by the generator model.

15. The non-transitory computer-readable storage medium according to claim 11, wherein the step of "randomly dividing the original data into initial sample point data and candidate sample point data, and constructing and training a generative adversarial network initial imputation model by utilizing the initial sample point data" comprises:

calculating and obtaining a missing matrix corresponding to a data missing state in the original data based on the acquired original data, wherein when a feature of the original data exists, the missing state of a corresponding position in the missing matrix is 1; and when the feature of the data matrix is missing, the missing state of the corresponding position in the missing matrix is 0;

dividing the original data into initial sample point data and candidate sample point data; and constructing and training a generative adversarial network initial imputation model based on the initial sample point data.

\* \* \* \* \*